United States Patent
Van Beek et al.

[11] Patent Number: 5,990,098
[45] Date of Patent: Nov. 23, 1999

[54] THERAPEUTIC USE OF 1-AMINO-3-(N,N-DIMETHYLAMINO)-PROPYLIDENE-1,1-BISPHOSPHONIC ACID AND ITS SALTS

[75] Inventors: Ermond R. Van Beek; Clemens W. G. M. Löwik; Socrates Papapoulos, all of Leiden, Netherlands; Rafael Labriola; Adriana Vecchioli, both of Pilar, Argentina

[73] Assignees: Gador, S.A., Argentina; University of Leiden, Netherlands

[21] Appl. No.: 08/983,247
[22] PCT Filed: Jul. 8, 1996
[86] PCT No.: PCT/EP96/02981
   § 371 Date: Sep. 1, 1998
   § 102(e) Date: Sep. 1, 1998
[87] PCT Pub. No.: WO97/02827
   PCT Pub. Date: Jan. 30, 1997

[30] Foreign Application Priority Data
Jul. 10, 1995 [EP] European Pat. Off. ............. 95110706

[51] Int. Cl.$^6$ .................. A01N 57/00; C07F 9/22
[52] U.S. Cl. .................. 514/114; 514/108; 514/102; 514/141; 562/13; 562/14
[58] Field of Search .................. 562/13, 14; 514/108, 514/114, 141, 102

[56] References Cited

U.S. PATENT DOCUMENTS 4,822,609  4/1989  Flora ..................... 424/112
5,668,120  9/1997  Shinoda et al. ............ 514/102

Primary Examiner—Gary Geist
Assistant Examiner—Taylor Victor Oh
Attorney, Agent, or Firm—Pendorf & Cutliff

[57] ABSTRACT

Use of 1-amino-3-N,N-dimethylamino)-propyliden-1,1-bisphosphonic acid of the structural formula:

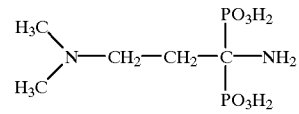

or of its monosodium or other pharmaceutically acceptable salt, as a biological carrier for bone active substances or for the preparation of a medicament for the diagnosis, prophylaxis and/or treatment of bone and/or mineral metabolism disorders.

18 Claims, 3 Drawing Sheets

THERAPEUTIC USE OF 1-AMINO-3-(N,N-DIMETHYLAMINO)-PROPYLIDENE-1,1-BISPHOSPHONIC ACID AND ITS SALTS

This application is the national phase of PCT/EP96/02981 filed Jul. 8, 1996.

BACKGROUND OF THE INVENTION

1. Field of the Invention

Bisphosphonates—synthetic compounds containing two phosphonate groups bound to a carbon and two additional groups $R_1$ and $R_2$, respectively (see formula A herebelow)—bind strongly to calcium crystals, inhibit their growth, suppress bone resorption and are used in the treatment of a variety of disorders of calcium and bone metabolism. It is generally considered that the "bone hook" (P-C-P with $R_1$) is responsible for the binding of these molecules to mineralized matrices, while, in turn, the $R_2$ group is primarily responsible for its effect on bone resorption.

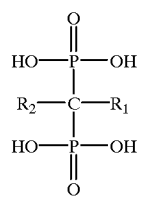

(A)

2. Description of the Related Art

U.S. Pat. No. 4,054,598 discloses a method with sequestering agents, especially for alkaline earth metal ions, having the formula 1-hydroxy-3-amino-alkane-1,1-bisphosphonic acids, useful for the treatment of disturbances of calcium or phosphate metabolism characterized by abnormal deposition of difficultly soluble calcium salts or the abnormal dissolution of hard tissues causing losses of hard bone substance, which cannot be replaced or only by incompletely crystallized tissues, such as Paget's disease, lithiasis, arthritis and others. Spanish Patent No. P910088 discloses pharmaceutical liposome preparations containing bisphosphonates as active compounds. The use of olpadronate as an anabolic agent for the treatment of osteoporosis and other bone metabolism disorders is claimed in the Applicant's earlier PCT application PCT/EP95/05142.

A number of 1,3-diaminoalkane-1,1-bisphosphonic acids including, amongst others, 1-amino-3-(N,N-dimethylamino)-propyliden-1,1-bisphosphonic acid are disclosed in DE-A1-25 34 390. Several applications (medical and non-medical), unrelated to the claimed methods of use of the present application, are mentioned, without giving any specific advantages for 1-amino-3-(N,N-dimethylamino)-propyliden-1,1-bisphosphonic acid.

DE-A1-18 13 659 is directed to compositions for the inhibision of deposition and mobilisation of calcium phosphate in tissues with an effective, but non-toxic content of various polyphosphonates. However, the specific compound of the present application is not mentioned.

In Eur. J. Clin. Invest. 1970, Vol. 1 (1) pp. 12–18 (Fleisch et al.) the inhibitory effect of phosphonates on the formation of calcium phosphate crystals in vitro and an aortic and kidney calcification in vivo is described. However, the specific compound of the present application is not mentioned.

DE-C1-10 02 355 is directed to processes for the production of various bisphosphonates. However, the specific compound of the present application is not mentioned. Moreover, no specific applications for the described compounds are given.

Z. Anorg. Allg. Chem. 389, pp. 119–128 (1972) (Plöger et al.) is directed to different processes for the production of various bisphosphonates, however without mentioning the specific compound of the present application or any specific application of the described compounds at all.

CA-A1-21 20 538 discloses the use of bisphosphonic acid derivatives for promoting bone repair. Although the general formula would also cover the specific compound of the present application, this compound or any related advantages are not mentioned in the description.

It is the object of the invention to provide for specific new medical applications of 1-amino-3-(N,N-dimethylamino)-propyliden-1,1-bisphosphonic acid or its monosodium or other pharmaceutically acceptable salt.

SUMMARY OF THE INVENTION

The present invention is related to the use of 1-amino-3-(N,N-dimethylamino)-propyliden-1,1-bisphosphonic acid of the structural formula

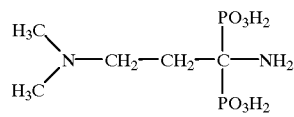

or of its monosodium or other pharmaceutically acceptable salt, as a biological carrier for other bone active substances.

In a preferred embodiment, said other bone-active substance is selected from the group consisting of cytokines, growths factors, prostaglandins, hormones and cytostatic drugs.

Furthermore the invention is related to the use of of 1-amino-3-(N,N-dimethylamino)-propyliden-1,1-bisphosphonic acid of the structural formula, in particular for the diagnosis, prophylaxis and/or treatment of urolithiasis, ectopic calcifications, all forms of osteoporosis, all forms of arthritis and all forms of periodontal diseases.

For further improvement of those methods of use, the invention proposes the simultaneous or sequential administration of at least one calcium salt and/or vitamin D or derivatives thereof and/or at least one fluoride salt and/or at least one parathyroid hormone and/or at least one androgen and/or at least one estrogen.

For showing the specific advantages of 1-amino-3-(N,N-dimethylamino)-propyliden-1,1-bisphosphonic acid, allowing the novel medical applications of this compound, the present inventors have provided for comparative examples with structurally closely related bisphosphonates as submitted in the following description. For that purpose, the hydroxyl group in $R_1$ of formula (A) of three clinically useful bisphosphonates, namely etidronate(1-hydroxyethyliden-1,1-bisphosphonate), pamidronate(1-hydroxy-3-aminopropyliden-1,1-bisphosphonate), and olpadronate(1-hydroxy-3(N,N-dimethylamino)-propyliden-1,1-bisphosphonate) was substituted by the amino group resulting in the following compounds: 1-aminoethyliden-1,1-bisphosphonic acid, 1,3-diaminopropyliden-1,1-bisphosphonic acid, and the specific compound of the present application 1-amino-3-(N,N-dimethylamino)-propyliden-1,1-bisphosphonic acid.

Etidronate and pamidronate were obtained by a process known from Argentine Patent No. 200,473 that discloses a process for the preparation of 1-hydroxyalkyliden-bisphosphonic acids and their salts, and Argentine Patent No. 218,558 that discloses a process to prepare 3-amino-1-hydroxypropylidene-bisphosphonic acids and their salts. Olpadronate is obtained by a process described in above-mentioned, unpublished PCT application No. PCT/EP95/05142. The amino substituted compounds were obtained by a synthesis process described hereinbelow (see examples 1 to 3).

The bisphosphonates with an amino substitution at $R_1$ exhibited physicochemical properties (binding to bone mineral, inhibition of calcium incorporation to bone, inhibition of crystal growth) comparable to their respective hydroxyl analogs (see Example 4 to 7).

1-amino-3-(N,N-dimethylamino)-propyliden-1,1-bisphosphonic acid (referred to as compound X) was, however, additionally devoid of any antiresorptive activity, which is the essential feature for the new medical applications of this compound. Compound X can therefore be used in the treatment of conditions in which a potent antiresorptive action is unwanted while targeting to calcium crystals and/or retention of other properties is required. Examples include the diagnosis, prophylaxis and/or treatment of urolithiasis, ectopic calcifications, their use as specific carriers for other bone active molecules (including, but not restricted to, cytokines, growth factors, prostaglandins, hormones, etc.) or cytostatic drugs to the skeleton, either for diagnosis of therapeutic purposes, or when the specific properties of the $R_2$ group on bone metabolism should be retained (e.g. anabolic effect) such as in the treatment of all forms of osteoporosis, all forms of arthritis and periodontal diseases.

DETAILED DESCRIPTION OF THE INVENTION

EXAMPLE 1

Figure 1:
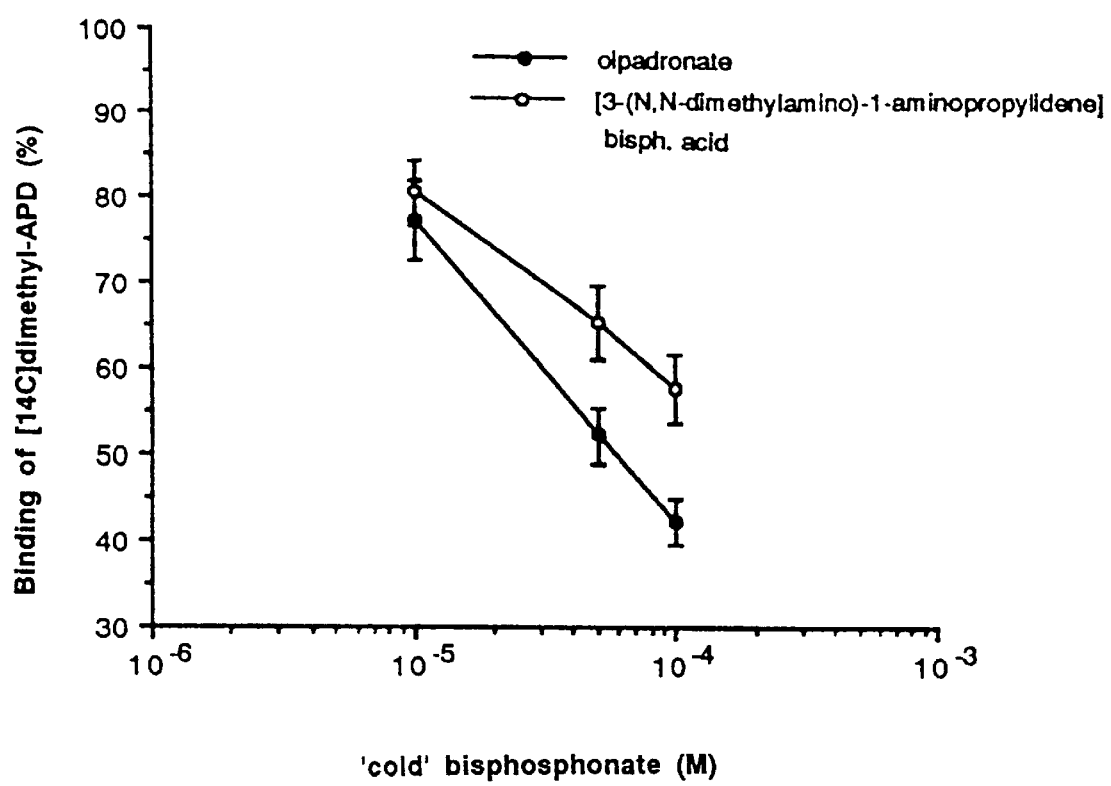
FIG. 1 shows the results of binding tests to bone mineral.

Synthesis of 1-amino-ethyliden-1,1-bisphosphonic acid (compound III) and monosodium salt (compound IV)

a. Mix 84 ml of water with 150 ml of phosphorus trichloride. Phosphorus acid (I) is formed.
b. Heat I to 130° C. and add 20 ml of acetonitrile. Maintain the temperature during 12 hours.
c. Cool to room temperature and add 250 ml of methanol.
d. Cool to 0–5° C., filter, wash with methanol and dry. The yield is 21.2 g (26%) of a colorless product with melts at 263° C. with decomposition (II).
e. Suspend the product in 43 ml of water. Add a solution of 4.4 g of sodium hydroxide in 15 ml of water and heat to 60° C. At this point, the product dissolves and a crystalline colorless precipitate is formed. Cool, filter, wash with water and dry. The yield is 34.9 g of the monosodium salt (IV).
f. To convert IV in the acid form (III), suspend 10.2 g of the salt in 90 ml of water. Add 4.2 g of sodium hydroxide and heat to 70° C. until total dissolution. Add concentrated hydrochloric acid until pH=1 (approximately 10 ml), cool, filter and wash with cold water. The yield is 9,34 g (100%) of colorless crystals which melt at 254–255° C. with decomposition.

Compound III 1-amino-ethyliden-1,1-bisphosphonic acid

Molecular Formula: $C_2H_9NO_6P_2$

Molecular Weight: 205,995

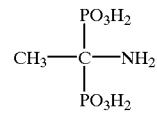

Elemental Analysis: Found: C: 13,33% H: 4,73% N: 6,78% Calculated: C: 11,66% H: 4,89% N: 6,80%

Spectral Properties:

$^1$H-NMR: Solvent: $D_2O/D_2SO_4$ Equipment: BRUCKER AC-200

| Chemical Shifts (ppm) | Multiplicity | Number of protons | ASSIGNMENTS |
|---|---|---|---|
| 2, 21 | t | 3 | $CH_3$ $^3J_{H-P} = 14, 5$ Hz |

EXAMPLE 2

Synthesis of 1,3-diamino-propylidene-1,1-bisphosphonic acid, monosodium salt (compound VII)

a. Add 39 ml of phosphorous tribromide to a suspension of 11.59 g of 3-aminopropionitrile and 8.93 g of phosphorous acid in 80 ml of dioxane of 40° C. Heat to 75–80° C. and maintain that temperature during 7 hours.
b. Add 36 ml of water and heat under reflux during 2.5 hours.
c. Cool to 5° C. and filter from an orange impurity.
d. Add 125 ml of isopropanol to solid and stir during 15 hours. Filter and dry. The yield is 1.43 g of a colorless solid that by suspension in water and filtration gives 783 mg of a solid which melts at 258–265° C. (V).
e. Suspend V in 2.5 ml of water, add 0.244 g of sodium hydroxide, which produces dissolution.
f. Add 7 ml of methanol. A white solid is produced (VI). Filter at 0° C. and dissolve in 1.5 ml of water.
g. Add 7 ml of methanol, cool to 5° C. filter and dry at 40° C. The yield is 800 mg of a colorless solid (VII), homogeneous by thin layer chromatography, which does not melt at 320° C.

Compound VII 1,3-diamino-propylidene-1,1-bisphosphonic acid, monosodium salt

Molecular Formular: $C_3H_{11}N_2O_6P_2Na$

Molecular Weight: 256,067

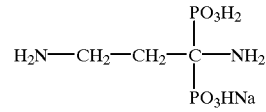

Spectral Properties:

$^1$H-NMR: Solvent: $D_2O/D_2SO_4$ Equipment: BRUCKER AC-200

| Chemical Shifts (ppm) | Multiplicity | Number of protons | ASSIGNMENTS |
|---|---|---|---|
| 2, 19 | m | 2 | —$CH_2$—C—P |
| 3, 32 | m | 2 | N—$CH_2$—C |

EXAMPLE 3

Synthesis of 1-amino-3-(N,N-dimethylamino)-propylidene-1,1-bisphosphonic acid (compound X)

a. Add 174.5 ml of phosphorous trichloride to a solution of 57.5 ml of N,N-dimethylaminopropionitrile in 102 ml of 70% methanesulfonic acid at room temperature.
b. Heat under nitrogen to 65° C. during 6 hours.
c. Cool to approximately 25° C., add 200 ml of water, heat under reflux during 5 hours and filter to eliminate a yellow solid in suspension (VIII).
d. Add 1.3 l of isopropanol to the filtrate with stirring. Cool to 0° C. and filter.
e. Suspend the solid in isopropanol:water (6:4), filter again and dry. The yield is 28.3 g (21.7%) of a colorless solid (IX).
f. Suspend IX in 56 ml of water. Add a solution of 4.5 g of sodium hydroxide in 30 ml of water, heat to 80° C. and filter while hot.
g. Add concentrated hydrochloric acid to the filtrate until pH=1 (about 13.5 ml), cool and filter.
h. Dissolve the solid in a solution of 3.4 g of sodium hydroxide in 60 ml of water at 65° C.
i. Add concentrated hydrochloric acid to pH=1, cool to 0° C., filter and dry. The yield is 20,6 g (73%) of colorless crystals which melt at 275° C. with decomposition (X).

Compound X 1-amino-3-(N,N-dimethylamino)-propyliden-1,1-bisphosphonic acid

Molecular Formular: $C_5H_{16}N_2O_6P_2$

Molecular Weight: 262,148

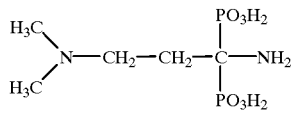

Elemental Analysis: Found: C: 23,44% H: 7,41% N: 10,11% Calculated: C: 22,91% H: 6,15% N: 10,69%

Spectral Properties:

$^1$H-NMR: Solvent: $D_2O/D_2SO_4$ Equipment: BRUCKER AC-200

| Chemical Shifts (ppm) | Multiplicity | Number of protons | ASSIGNMENTS |
|---|---|---|---|
| 9, 41 | s | 1 | $^+$N—H |
| 2, 65 | bt | 2 | $CH_2$—N |
| 2, 05 | s | 6 | $CH_3$—N—$CH_3$ |
| 1, 71–1, 48 | m | 2 | $CH_2$—C—P |

EXAMPLE 4

Binding to Bone Mineral

Binding of compounds (III), (VII) and (X) with an amino group at $R_1$ to bone was examined by their ability to displace 14C-bisphosphonate from mouse fetal explants according to accepted methodology (van Beek et al, Journal of Bone and Mineral Research, (1994), Vol. 9, p. 1875–1882) and was compared to that of their hydroxyl analogs, the bisphosphonates etidronate, pamidronate and olpadronate.

All six bisphosphonates tested bound to the explants dose-dependently. There were no differences between etidronate and compound (III) and pamidronate and compound (VII) and olpadronate and compound (X). The results are shown in FIG. 1.

EXAMPLE 5

Figure 2:
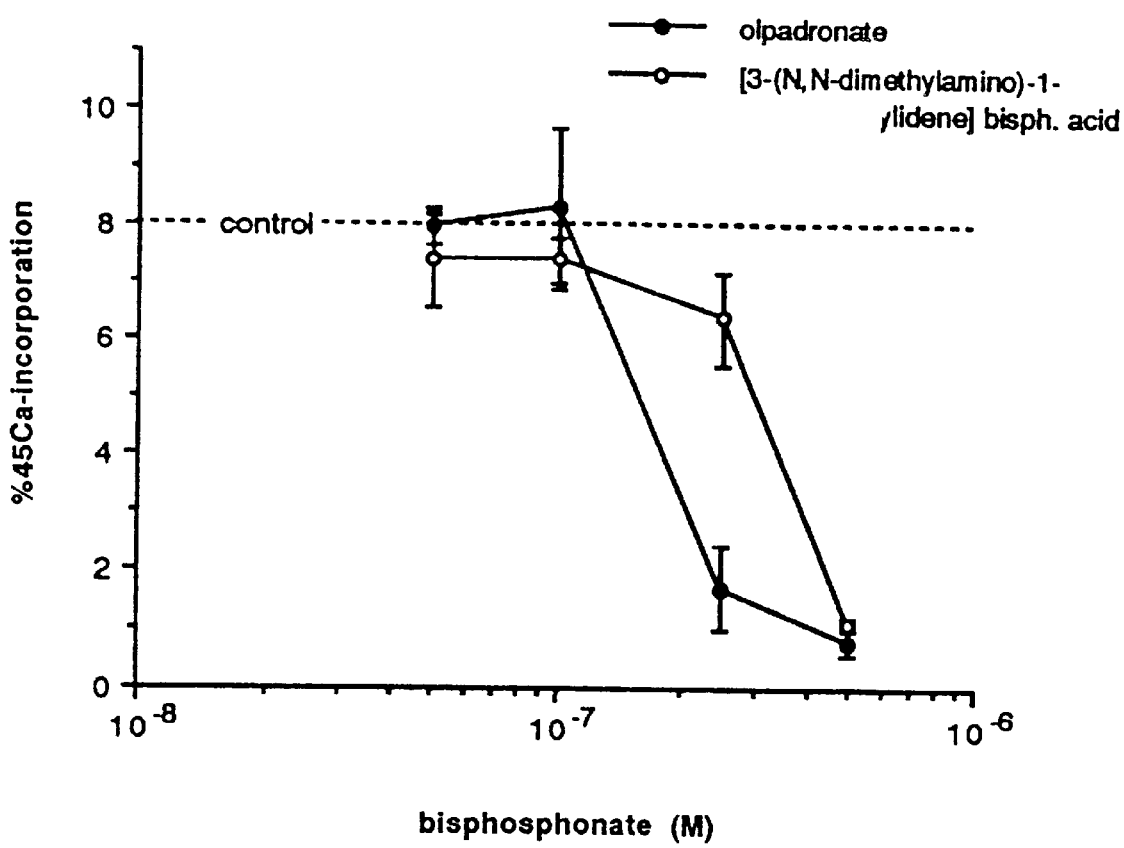
FIG. 2 shows results of test on inhibition of 45 calcium incorporation into osteoplast-devoid bones.

Inhibition of 45 Calcium Incorporation Into Osteoclast-Devoid Bones 45 calcium incorporation into osteoclast-devoid fetal bones of mice was inhibited by all bisphosphonates dose-dependently. There were no differences between the three hydroxybisphosphonates (etidronate, pamidronate and olpadronate) and their respective aminosubstituted analogs (compound III, VII, and X). Half-maximal inhibiting concentrations: etidronate and compound III: $1.5 \times 10^{-7}$ M; pamidronate and compound VII: $2 \times 10^{-7}$ and $2.5 \times 10^{-7}$ M, respectively; olpadronate and compound X: $2 \times 10^{-7}$ and $4 \times 10^{-7}$ M, respectively. The results are shown in FIG. 2.

EXAMPLE 6

Inhibition of Crystal Growth

Olpadronate and compound X were also tested (Methode: Kok et al., Kidney Int. 1988, Vol. 34, p. 346–350) for their ability to inhibit the growth of calcium oxalate monohydrate crystals using a seeded crystal growth system. Both compounds inhibited the growth of the calcium crystals roughly equipotently (half-maximal concentrations: $6 \times 10^{-6}$ M and $3 \times 10^{-6}$ M, respectively).

EXAMPLE 7

Inhibition of Bone Resorption

Fetal mouse metacarpal bones prelabelled with 45 calcium were treated with various concentrations of the six bisphosphonates tested in the previous experiments, and were cultured for 10 days. Resorption was assessed as percentage of 45 calcium release relative to control according to standard methodology (Van der Pluijm et al., Endocrinology, (1991), Vol. 129, p. 1596–1604).

Figure 3:
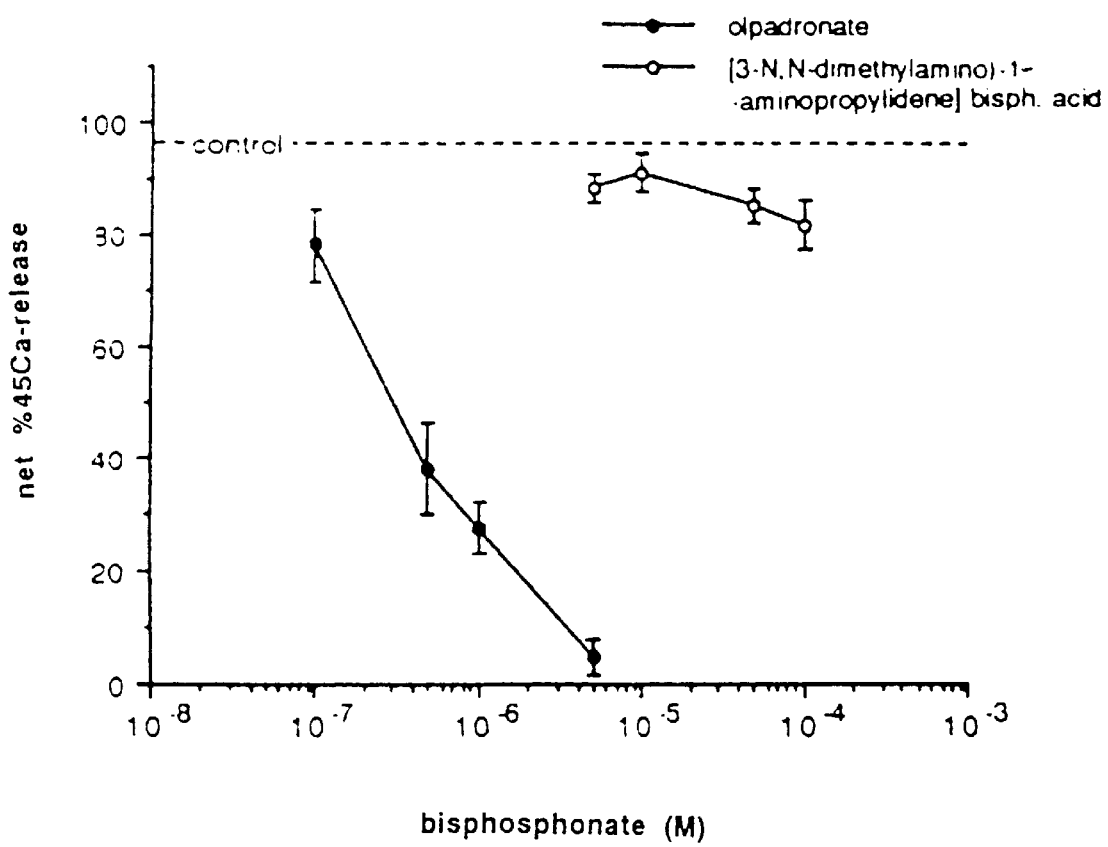
FIG. 3 shows the inhibition of bone resorption.

Etidronate and its analogous compound III suppressed 45 calcium release equipotently; pamidronate was about 6 times more potent than compound VII, while compound X showed absolutely no antiresorptive activity in contrast to the increased potency of olpadronate. The results are shown in FIG. 3.

According to previous results (Papapoulos et al., Journal of Bone and Mineral Research, 1989, Vol. 4, p. 775–781) those in vitro data allow prediction of equivalent in vivo effects.

The inventive features disclosed in the preceding description, as well as in the claims and drawings can be essential to the realization of the invention in its various embodiments, either singly or in the form of random combinations.

What is claimed is:

1. A bone-active composition comprising a bone-active substance and a biological carrier for said bone active substance, wherein said biological carrier is a 1-amino-3-(N,N-dimethylamino)-propylidene-1,1-bisphosphonic acid having the structural formula:

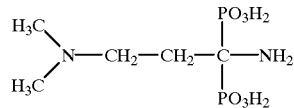

or its monosodium or other pharmaceutically acceptable salt.

2. A composition according to claim 1, wherein said other bone-active substance is selected from the group consisting of cytokines, growths factors, prostaglandins, hormones, glycine or other amino acids or modified amino acids and cytostatic drugs.

3. A pharmaceutical composition for the diagnosis, prophylaxis and/or treatment of bone and/or mineral metabolism disorders, said composition comprising a bone active substance and a biological carrier for said bone-active substance, wherein said biological carrier is a 1-amino-3-(N,N-dimethylamino)-propylidene-1,1-bisphosphonic acid having the structural formula:

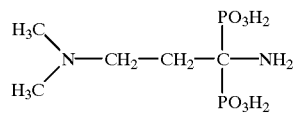

or its monosodium or other pharmaceutically acceptable salt.

4. A composition according to claim 3 wherein said composition is for the diagnosis, prophylaxis and/or treatment of urolithiasis, ectopic calcifications, all forms of osteoporosis, all forms of arthritis and all forms of periodontal diseases.

5. The composition according to claim 1, comprising at least one calcium salt.

6. The composition according to claim 1, comprising vitamin D or derivatives thereof.

7. The composition according to claim 1, comprising at least one fluoride salt.

8. The composition according to claim 1, comprising at least one parathyroid hormone.

9. The composition according to claim 1, comprising at least one androgen.

10. The composition according to claim 1, comprising at least one estrogen.

11. A method for diagnosing prophylaxis, or treating bone and/or mineral metabolism disorders, said method comprising administering to a patient suffering from bone and/or mineral metabolism disorders an effective amount of a bone active substance and a biological carrier for said bone active substance, wherein said biological carrier is a 1-amino-3-(N,N-dimethylamino)-propylidene-1,1-bisphosphonic acid having the structural formula:

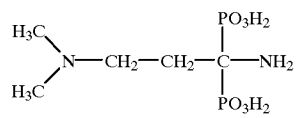

or its monosodium or other pharmaceutically acceptable salt.

12. A method as in claim 11, wherein said diagnosis, prophylaxis and/or treatment is selected from the group consisting of urolithiasis, ectopic calcifications, all forms of osteoporosis, all forms of arthritis and all forms of periodontal diseases.

13. A method as in claim 11, further comprising the simultaneous or sequential administration of at least one calcium salt.

14. A method as in claim 11, further comprising the simultaneous or sequential administration of vitamin D or derivatives thereof.

15. A method as in claim 11, further comprising the simultaneous or sequential administration of at least one fluoride salt.

16. A method as in claim 11, further comprising the simultaneous or sequential administration of at least one parathyroid hormone.

17. A method as in claim 11, further comprising the simultaneous or sequential administration of at least one androgen.

18. A method as in claim 11, further comprising the simultaneous or sequential administration of at least one estrogen.

* * * * *